(12) United States Patent
Gaschino et al.

(10) Patent No.: US 7,278,998 B2
(45) Date of Patent: Oct. 9, 2007

(54) ACTUATING DEVICE FOR CATHETERS

(75) Inventors: Paolo Gaschino, Castagneto Po (IT); Laura Ghione, Turin (IT); Maria Curcio, Saluggia (IT); Giovanni Rolando, Chivasso (IT)

(73) Assignee: Sorin Biomedica Cardio S.r.l., Saluggia (Vercelli) (IT)

( * ) Notice: Subject to any disclaimer, the term of this patent is extended or adjusted under 35 U.S.C. 154(b) by 473 days.

(21) Appl. No.: 10/761,950

(22) Filed: Jan. 21, 2004

(65) Prior Publication Data

US 2004/0153137 A1 Aug. 5, 2004

(30) Foreign Application Priority Data

Jan. 24, 2003 (IT) .......................... TO2003A0037

(51) Int. Cl.
*A61F 2/04* (2006.01)
(52) U.S. Cl. ....................................... 606/108; 623/1.11
(58) Field of Classification Search ....... 623/1.11–1.12
See application file for complete search history.

(56) References Cited

U.S. PATENT DOCUMENTS

| 5,201,757 | A | | 4/1993 | Heyn et al. |
| 5,611,813 | A | * | 3/1997 | Lichtman .................... 606/205 |
| 5,968,052 | A | * | 10/1999 | Sullivan et al. ............. 623/1.11 |
| 6,019,778 | A | | 2/2000 | Wilson et al. |
| 6,146,415 | A | | 11/2000 | Fitz |
| 6,238,402 | B1 | | 5/2001 | Sullivan, III et al. |
| 6,371,963 | B1 | * | 4/2002 | Nishtala et al. ............. 606/113 |
| 6,375,676 | B1 | | 4/2002 | Cox |
| 6,391,051 | B2 | | 5/2002 | Sullivan, III et al. |
| 6,402,760 | B1 | * | 6/2002 | Fedida ........................ 606/108 |
| 6,527,779 | B1 | * | 3/2003 | Rourke ....................... 606/108 |
| 6,599,296 | B1 | | 7/2003 | Gillick et al. |
| 6,602,280 | B2 | * | 8/2003 | Chobotov ................... 623/1.11 |
| 6,755,854 | B2 | * | 6/2004 | Gillick et al. .............. 623/1.11 |
| 7,052,511 | B2 | * | 5/2006 | Weldon et al. ............. 623/1.11 |
| 2002/0177789 | A1 | * | 11/2002 | Ferry et al. ................. 600/585 |
| 2003/0028236 | A1 | | 2/2003 | Gillick et al. |
| 2004/0006380 | A1 | | 1/2004 | Buck et al. |

FOREIGN PATENT DOCUMENTS

| DE | 198 19 634 A1 | 11/1999 |
| EP | 1 302 178 A2 | 4/2003 |
| EP | 1 302 178 A3 | 4/2003 |
| WO | WO 00/10486 | 3/2000 |

OTHER PUBLICATIONS

European Search Report in European Application No. 03029555.4 (3 pages).

* cited by examiner

*Primary Examiner*—Glenn K. Dawson
(74) *Attorney, Agent, or Firm*—Popovich, Wiles & O'Connell, P.A.

(57) ABSTRACT

An actuating device for a catheter comprising at least one first part and one second part, which are able to more relative to each other, the actuating device comprising: (i) a slide which can be connected to one of said first part and said second part of the catheter; (ii) a slider, which can be actuated for moving said slide and moving said first part and said second part relative to each other; and (iii) a speed-change mechanism, which is set between said slider and said slide.

15 Claims, 6 Drawing Sheets

ACTUATING DEVICE FOR CATHETERS

BACKGROUND OF THE INVENTION

The present invention relates to devices for actuating catheters.

Devices for actuating catheters are described in U.S. Pat. Nos. 6,391,051 B2; 6,375,676 B1; 6,238,402 B1; 6,146,415; 6,019,778; 5,201,757; and also in WO 00/10486 and DE 198 19 634 A1. The catheters described in these documents are to a major extent designed to be used for placing and splaying out in situ stents, such as stents for angioplasty, in particular stents of the self-expanding type. With a certain degree of simplification, but with substantial adherence to the actual situation, it may be stated that, in the solutions considered above, the relative movement designed to disengage the stent from the element or elements that the keep it in a radially contracted condition is left practically completely to the control of the operator. In particular, the speed for carrying the operation out is left to the control of the operator.

Clinical experience developed in the use of stents of this nature demonstrates, however, that this method is not altogether free from drawbacks. It is found, for example, that the action of splaying out the stent (performed gradually at one end of the stent and then involving the stent as a whole) must usually be performed in its initial steps in a delicate and gradual way. Precisely in these initial steps, the operator must, however, overcome quite a high initial force of friction, represented by the need to overcome the resistance opposed by the means of containment of the stent. Usually, these means of containment consist of a tubular tunic fitted on the stent that must be retracted by causing it to slide axially on the stent so as to uncover and gradually free the stent itself.

It may happen that the force applied by the operator in the initial step of the operation of splaying out, in a way commensurate with the need to start the movement of retraction of the tunic with respect to the stent, will be excessive in the subsequent steps of splaying out. All this entails possible adverse effects, above all when the stent in question is a stent for coronary angioplasty of small axial length, for example about ten millimetres. In the case of stents of a substantial axial length (for instance, certain peripheral stents), it may instead happen that the movement of disengagement of the tunic from the stent will end up being executed at an excessively slow speed.

There is a need in the art to provide a guide for the operator in carrying out the operation of splaying out the stent precisely by the device for actuating the catheter, thus preventing the criteria whereby the operation is carried out from being entrusted altogether to the operator. The present invention provides a device for actuating catheters that will be able to overcome the drawbacks referred to previously and to meet the aforesaid need to allow the criteria with which the operation is carried out to be left totally to the operator.

It will be appreciated that in the definition of the invention, reference is made herein to actuating catheters understood in a general sense. Even though the present invention has been developed with particular attention paid to its possible use for actuating catheters for the application of stents, and in particular self-expanding stents, it may be used to advantage together with catheters of any type in which it is in any case necessary, for use of the catheter, to perform a relative movement of parts of the catheter itself.

The invention will now be described, purely by way of non-limiting example, with reference to the annexed drawings.

DETAILED DESCRIPTION OF THE INVENTION

In the figures the reference number 1 designates as a whole a device which can be used for actuating a catheter (not illustrated as a whole) comprising two parts, upon which, in the stage of use of the catheter itself, it is necessary to impart a relative movement. Just to provide an example, and with reference to the field of use of the device 1 currently considered as being preferential, the catheter in question may consist of a catheter for implantation and splaying out in situ of stents of the self-expanding type. An extended illustration of the characteristics of stents of this nature and of the corresponding catheters is provided in the documents of the known art listed in the introductory part of the present description.

As regards the purposes of the present application, in what follows it will be assumed that the parts of the catheter upon which it is necessary to impart a relative movement are constituted by: (i) a filiform guide element T, consisting typically of a microtube, which is in turn designed to slide on the so-called guide wire of the catheter itself; and (ii) a sheath or tunic G mounted on the element T so as to be able to slide longitudinally along the element T itself. In the course of the ensuing description it will be assumed that the relative movement in question must take place between a first relative position, in which the sheath or tunic G occupies an advanced position with respect to the element T, and a second position in which, as a result of a movement of recession with respect to the element T, the sheath G recedes and uncovers, enabling its splaying-out, a self-expanding stent fitted to the distal end of the element T. All this occurs, as has already been said, according to criteria that are widely known in the art.

Figure 2:
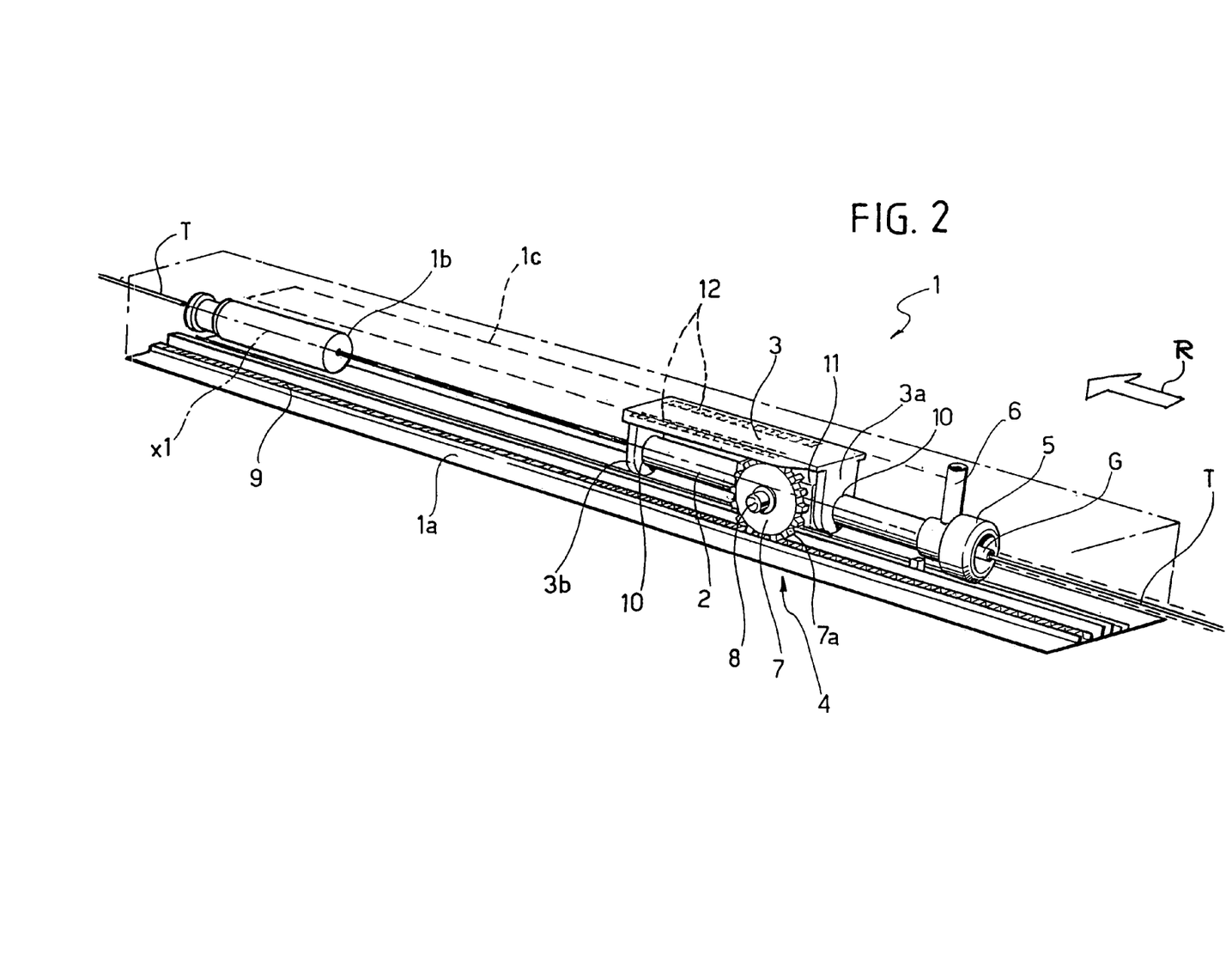

For the present purpose, the function of the device 1 illustrated herein is to enable the sheath or tunic G to perform, with respect to the element T, a travel of recession in the direction of the arrow designated by R in FIG. 2. Persons skilled in the art will appreciate immediately the fact that the aforesaid movement is to be viewed basically as a relative movement between the element T and the sheath or tunic G.

The solution described in what follows usually envisages in fact that the sheath or tunic G will perform a movement of recession with respect to the element T, which is kept in a position that is substantially fixed with respect to the casing of the device 1, with simple kinematic variants (within the reach of a person skilled in the sector). The solution described herein can be adapted so as to obtain the complementary result; enabling the tubular element T to advance with respect to the sheath G, which is kept in a position substantially fixed with respect to the casing of the device 1, or cause the travel of relative displacement in the direction of the arrow R to be obtained as a result of a combined movement both of the sheath or tunic G and of the element T.

Previously, implicit reference was made to a situation in which it is assumed that the stent (not illustrated) is fitted on the element T and there withheld in a radially contracted position by the sheath or tunic G, so that the stent will expand as it disengages from the sheath or tunic G. The configuration of the distal end of the catheter could be such as to envisage an at least partly complementary arrangement: in either case, the details of construction of the distal end of the catheter are in themselves irrelevant for the purposes of understanding and implementing the solution described herein, the possibilities of use of which are altogether general.

It will moreover be appreciated that the sheath G is represented herein in a cutaway view so as to highlight how the travel of recession R is performed. It is in fact altogether evident that the sheath G extends with substantial continuity, coating the element T throughout its length up to the distal end of the catheter (not visible in the annexed drawings).

In the embodiment illustrated herein (which, it must be recalled, is nothing more than an example), it is envisaged that the device 1 has a containment casing having a generically elongated shape, represented herein with a dashed line, with the exception of the end wall, designated by 1a.

In a specific way, the figures of the attached drawings illustrate a device 1 with a casing having a shape that substantially may be likened to a parallelepiped. Provided that certain essential functional needs are respected, such as the possibility for the operator to gain access to the control members of the device, the shape of the aforesaid casing can be of any type whatsoever. In particular, this shape can be defined according to ergonomic criteria so as to enable a convenient grip and manipulation of the device 1 on the part of the operator who must use the device 1.

In the embodiment illustrated herein, the device 1 has one front end, the one in which the sheath G set on top of the element T is represented, and one rear end, opposite to the preceding one. In an area corresponding to the aforesaid rear end, the end wall 1a (or any other part of the casing of the device 1) carries a guide element, such as a bushing 1b functioning as supporting element for the element T. It will be appreciated that usually the element T is fixed to the guide element 1b so as to be in effect fixed to the casing of the device 1. This connection is designed to facilitate the operation of catheterization, performed according to known criteria (for example, resorting to the known techniques, such as "over the wire" technique or "rapid exchange" technique).

In basic terms, the solution described herein envisages the presence in the device 1 of three elements: (i) a slide 2, connected to the sheath G so as to enable it to be drawn along in the travel of recession in the direction of the arrow R; (ii) a slider 3, constituted by an element accessible from outside the casing 1, designed to enable the operator to control the movement of recession of the slide 2, to which the sheath G is connected; and (iii) a speed-change mechanism 4, kinematically set between the slide 2 and the slider 3 so as to provide at least two different drive ratios during the movement that causes the slide 2 to draw along with it the sheath G in the travel of recession in the direction of the arrow R.

In the embodiment illustrated herein, the slide 2 is basically constituted by a tubular element (preferentially made, like the other parts of the device 1, of a plastic material compatible with use in the medical or surgical fields, in particular in the sterile field), which is fitted on the element T so as to be able to slide longitudinally within the device 1 along an axis X1 corresponding in effect to the axis of the element T, which extends longitudinally within the casing of the device 1. Fixing of the front end of the tubular slide T to the sheath G is made in a position corresponding to a ring nut 5, to which there is usually associated a connection element 6 for flushing the catheter. Movement of the slide 2 along the axis X1 is rendered regular by the presence of a wheel, and preferably two wheels 7 mounted on hub parts 8, which project laterally from the body of the slide 2. The overall structure of the slide 2 illustrated herein may thus approximately be likened to the structure of a wheelbarrow or cart. The wheel or wheels 7 run in grooves 9 provided along the end wall 1a of the wall of the casing. For reasons that will emerge more clearly from what follows, the wheels 7 are in actual fact gearwheels, provided with an external toothing 7a designed to co-operate with a corresponding rack toothing, provided along the groove or grooves 9.

Figure 1:
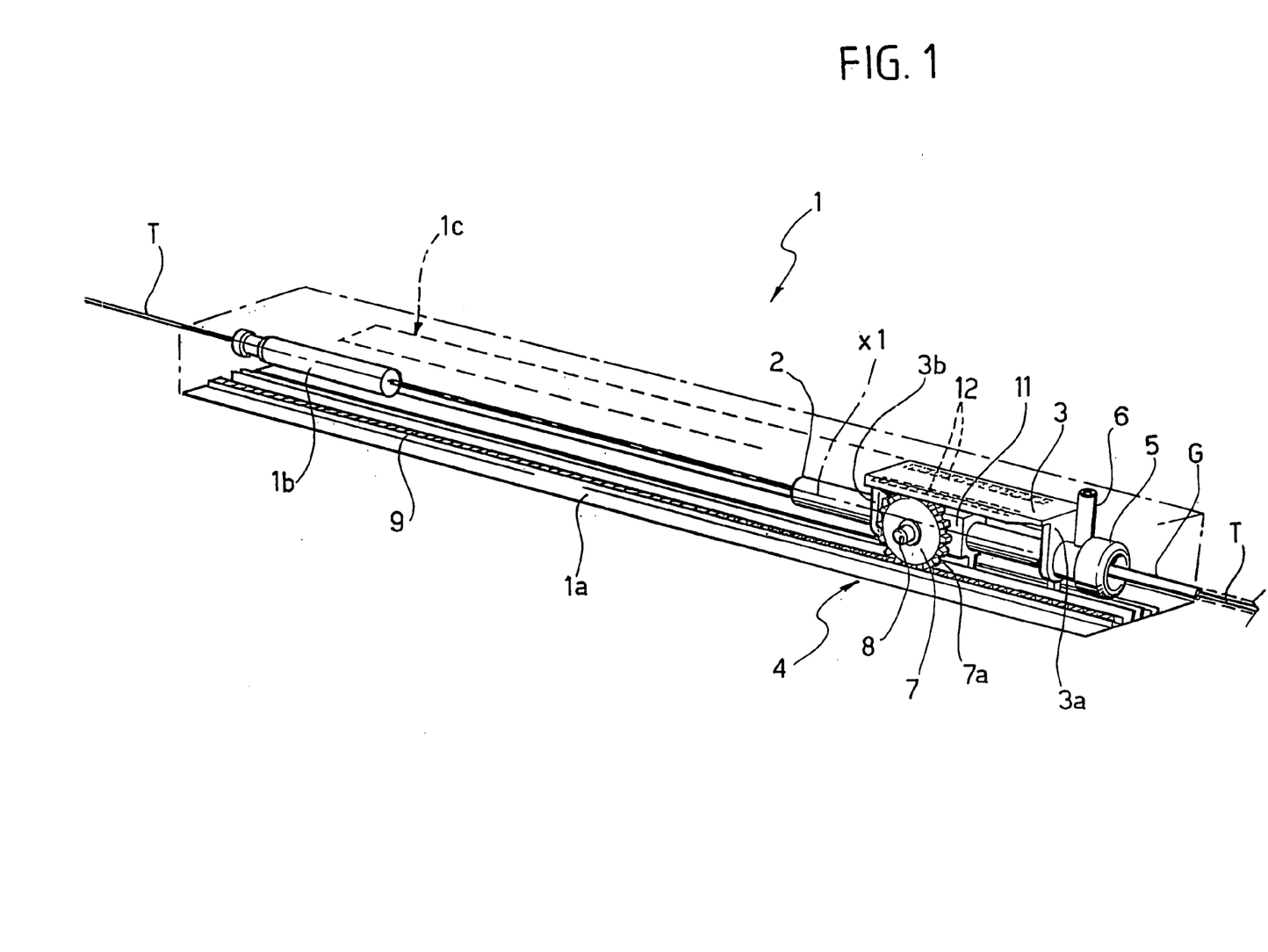
FIGS. 1 and 2 illustrate, in two perspective views that are substantially equivalent to one another, two different possible positions of operation of a device according to the invention.

In the exemplary embodiment illustrated herein, the slider 3 consists of a board which is able to move along a slit 1c provided in the top wall of the casing 1. In this way, the operator who actuates the catheter is able, for example, to grip the casing of the device 1 and to rest his thumb on the slider 3, maintained in the position illustrated in FIG. 1, the aim being to control gradually the recession of the slider 3 itself, as schematically illustrated in FIG. 2. Under closer examination, the slider 3 in actual fact has a gantry-shaped or II-shaped structure of which the board mentioned previously forms the web part. This web part carries at its end two side tab parts 3a and 3b, provided at their distal ends with openings 10 having a diameter slightly greater than the external diameter of the body of the slide 2. As may be immediately noted from the figures, the slider 3 can thus be fitted on the slide 2 so as to be mobile with respect to the slide 2 itself in the direction of the axis X1. In particular, this movement is performed between an advanced position, represented in FIG. 1, and a retracted position, represented in FIG. 2. These two positions are basically identified by bearing, respectively with the side part 3b and the side part 3a, upon a central prismatic core 11 of the slide 2. From the core 11 there branch off laterally the pins 8, on which the gearwheels 7 are mounted. Designated by 3a and 3b the side parts of the slider 3 face, respectively, the ring nut 5, where the sheath G is connected to the slide 2 and the bushing 1b, where the element T is fixed. The advanced position of the slider 3 is reached when the element 3b is bearing upon the prismatic core 11 (see FIG. 1), and the retracted position of the slider is instead reached when the element 3a is bearing upon the same prismatic element 11 (see FIG. 2).

Figure 3:
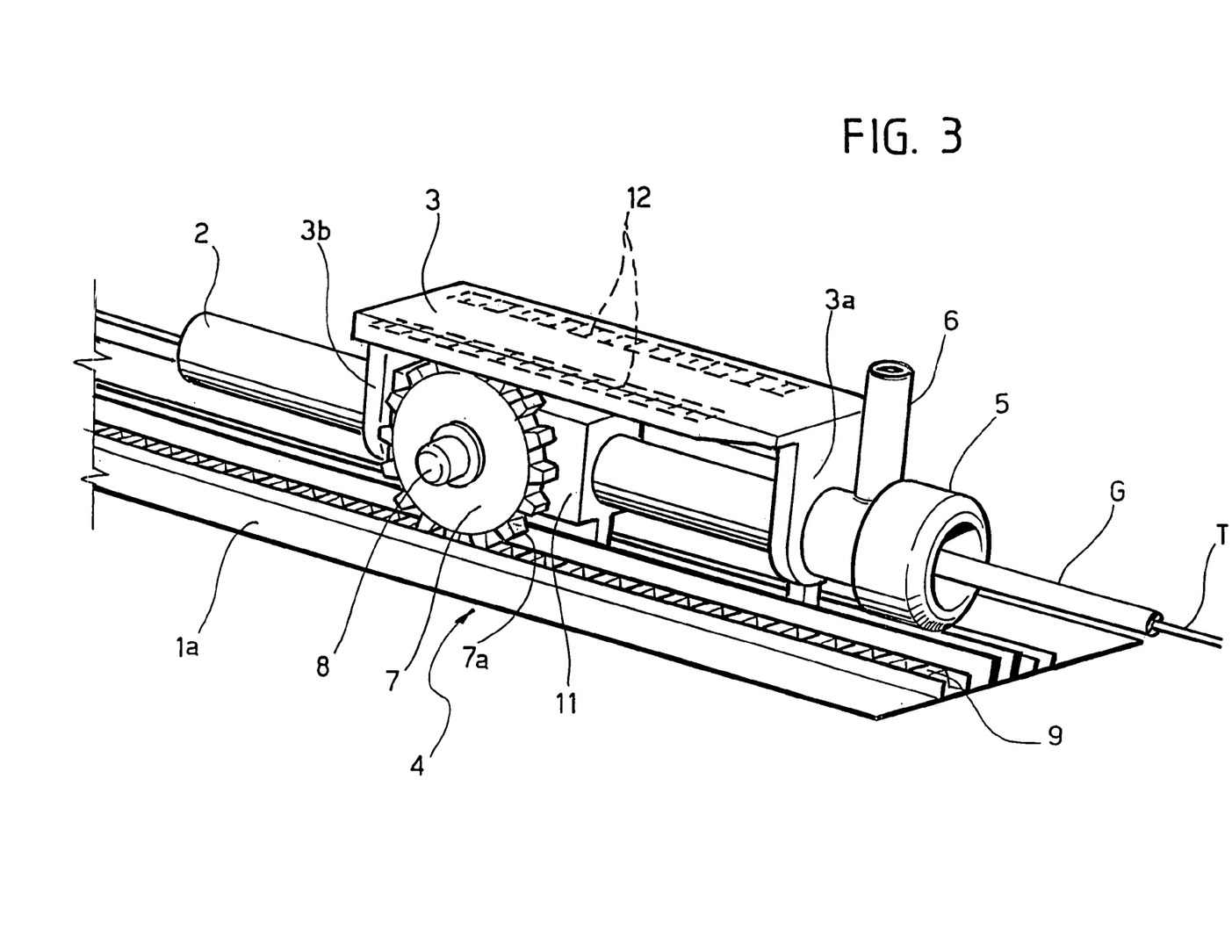
FIGS. 3, 4, and 5 illustrate, at a slightly enlarged scale, some details of the device of FIGS. 1 and 2, represented also in this case in different possible positions of operation.
Figure 4:
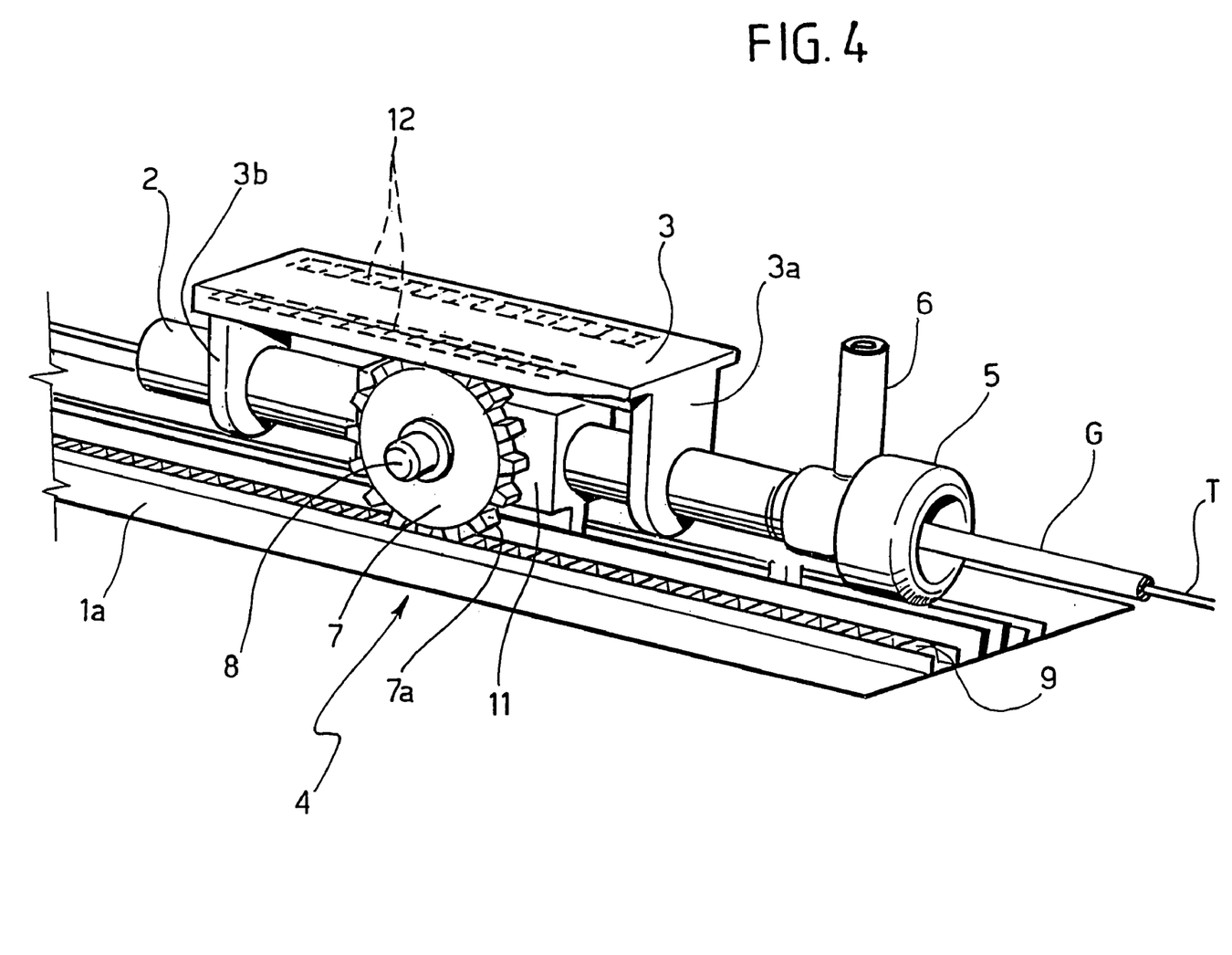

On the face of the board 3 of the slider facing the wheel or wheels 7 there are one or two rack guides 12. The guides 12 may substantially be likened to the guides 9, with the evident difference that their respective channel formations are open in opposite directions, towards one another. The main difference is, however, represented by the fact that, as will be appreciated better from the enlarged views of FIGS. 3 to 5, the rack or each rack 12 extends only at the rear end of the board part of the slider 3, whilst advancing towards the front end of the board 3 itself, the channel formations with the racks 12 assume simply the appearance of smooth-walled guide tracks which, in a preferred way, move away from the wheel or wheels 7, disengaging completely therefrom the external ring gear 7a.

The gearwheel or gearwheels 7 constitute the central element of the speed-change mechanism aimed at causing, in different portions of the travel of movement in the direction of the arrow R, the drive ratio between the slider 3 and the slide 2 to assume at least two distinct values. In particular, when the slider 3 is in the advanced position illustrated in FIG. 1, the gearwheel or gearwheels 7 are found with their external ring gear 7a meshing, respectively: (i) with a rack 9 provided in the end wall 1a of the casing 1; and (ii) with a rack 12 provided on the bottom wall of the board part 3 of the slider 1. In these conditions, between the slider 3 and the slide 2 there exists a drive ratio 1:2 in the sense that each unit length travelled by the slider 3 results in a homologous displacement of the slide 2 by an amount equal exactly to half of the distance travelled by the slider 3. This fact is evident since the pin or pins 8 are found in effect halfway between the racks 9 and 12. These conditions of operation are usually determined when, once the distal end of the catheter has been localized on the implantation site, there begins the operation of splaying out the stent by causing the sheath G to slide gradually and disengage the stent accordingly.

The presence of the aforesaid drive ratio, in the sense of a demultiplication, causes the movement imparted by the operator by acting on the board of the slider 3 to be subjected to demultiplication. This fact has a dual beneficial effect: (i) in the first place, the movement of retraction of the sheath or tunic G with respect to the element T is rendered extremely gradual, further increasing the delicacy with which this movement is brought about by the operator; and (ii) in the second place, the demultiplication of the amount of displacement results in an amplification (in practice, in a doubling) of the tensile force exerted by the slide 2 on the sheath G with respect to the homologous force exerted by the operator on the board part of the slider 3. This second effect is particularly beneficial because it reduces the effort that the operator needs to make to overcome the friction initially opposed by the sheath or tunic G to the movement of recession.

Figure 5:
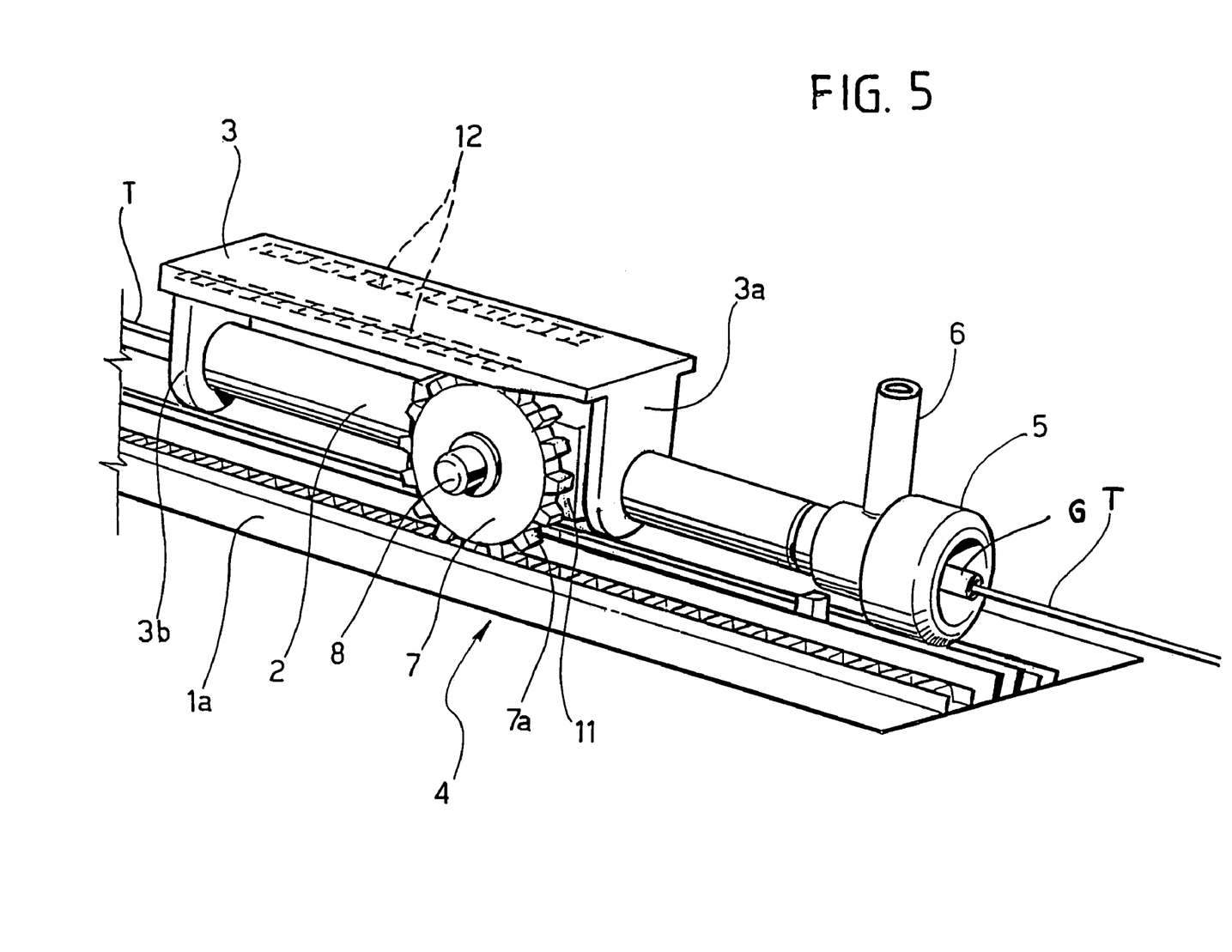

The conditions of kinematic coupling just described, with the ratio of demultiplication of the speed of displacement described previously, is maintained for a fair extent of the subsequent movement of recession of the slider 3 (see FIG. 4), until the condition represented in FIG. 5 is reached. This is a condition in which, simultaneously: (i) the side element 3a of the slider 3 is brought to bear upon the prismatic core 11 of the slide 2; and (ii) the wheel or wheels 7 are disengaged with their external toothing 7a from the rack or racks 12 provided on the bottom face of the board part of the slider 3. Once these conditions have been reached, the speed-change mechanism described starts to operate with unit drive ratio, in the sense that, receding further in the direction of the rear end of the device 1, the slider 3 pulls along with it the slide 2 by adopting, in this case, a unit drive ratio, so that the amount of travel and rate of displacement of the slider 3 and of the slide 2 are identical to one another.

In these conditions, given the same speed of displacement backwards of the slider 3 effected by the operator, the movement of recession of the sheath G (controlled by the slide 2, to which the sheath G is attached by means of the ring nut 5) is far more rapid than occurred previously, i.e., when the drive mechanism located between the slider 3 and the slide 2 applied the ratio of demultiplication described previously. The aforesaid condition of direct coupling between the slider 3 and the slide 2 is usually maintained up to completion of the travel of recession of the sheath G.

As already mentioned previously, the solution described herein can be developed by enabling the speed-change mechanism of the device to have a greater number of different speed ratios instead of having just two possible drive ratios (i.e., the first 50% demultiplication and the second direct-drive ratio). For example, above all in view of its use with stents having quite considerable longitudinal dimensions, it is possible to consider that, in addition to a first step of operation with a speed-demultiplication ratio and a second step of direct drive, the aforesaid speed-change mechanism will envisage a third step of operation with a speed-multiplication ratio, i.e., in conditions such that the movement of the slide 2 (and consequently the movement of retraction of the sheath G) will occur at a speed higher than the speed imparted by the operator upon the slider 3.

Once again, as an alternative or in addition to a speed-change mechanism with discrete ratios, it is possible to use, in the framework of a device of the type described, a speed-change device having a ratio that is variable in a continuous way.

These possible variant embodiments prove particularly attractive in the case where the aim is to enable the criteria with which the operation of splaying out the stent is performed to be removed, at least in part, from the direct control of the operator, the aim being to enable the operation in question, performed according to criteria in effect imposed by the actuating device of the catheter, to be performed in a repetitive way, determined according to uniform modalities, by different operators. Accordingly, it is understandable that the solution described herein may be implemented by resorting to speed-change mechanisms of any type known in the art and/or by modifying the functions of the various elements described previously.

For example, with reference to the same device structure illustrated in the annexed drawings, it is possible to hypothesize a variant embodiment in which the slide 2 and the slider 3 reverse their respective roles, envisaging that: (i) the sheath or tunic G will be connected, instead of to the slide 2, to the part 3a; and (ii) the pin or pins 8, and not the board part 3, will be associated to the slider designed to be actuated by the operator. In the first stage of operation, such a device would perform, instead of the function described previously (demultiplication of the speed imposed by the operator, with the slide 2 and the sheath G that move with a speed equal to half that applied to the slider 3 by the operator), an exactly opposite function of multiplication (with the part 3a and the sheath G connected thereto, which move at a speed twice that of the speed imposed by the operator on the pin or pins 8).

Figure 6:
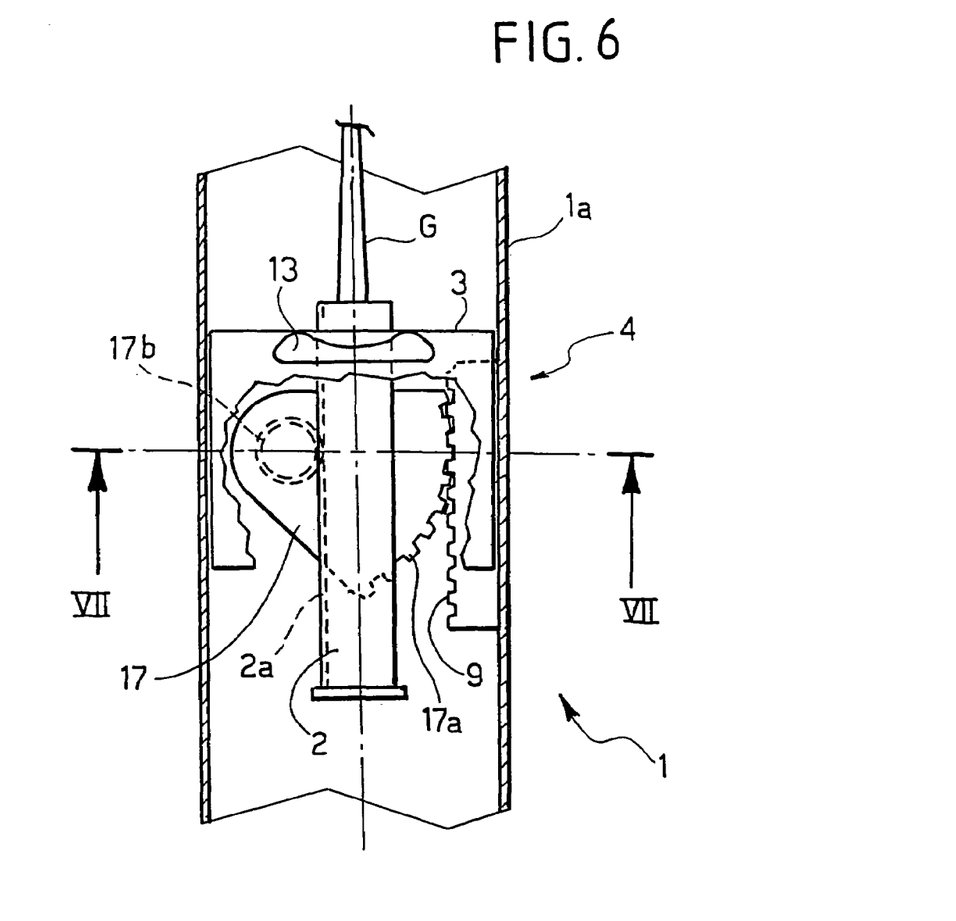
FIG. 6 illustrates a possible variant embodiment of the invention.
Figure 7:
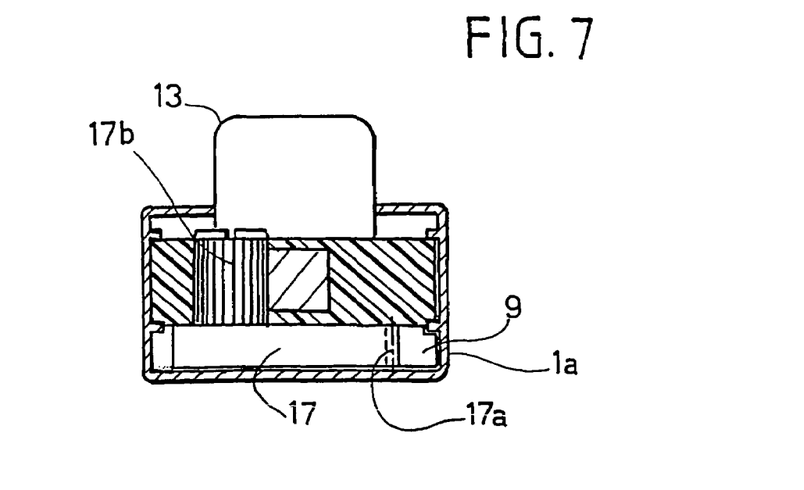
FIG. 7 is a cross-sectional view according to the line VII-VII of FIG. 6.

Yet another variant embodiment is illustrated in FIGS. 6 and 7, where parts that are identical or functionally equivalent to the ones described previously have been designated by the same reference numbers.

In the variant illustrated in FIGS. 6 and 7, the slider 3 is constituted by a sort of carriage which is able to move along the casing of the device under the action exerted by the operator by acting upon a tab 13 projecting on the outside of the casing itself. The carriage of the slider carries with it a toothed sector 17, which meshes, with its external toothing 17a, with the toothing or rack 9 provided on the wall 1a of the casing.

The toothed sector 17 (having for example an angular opening of approximately 50°) has a grooved central pin 17b, which has a dual function. Firstly, as a pin, it extends through the body of the slider 3 and causes the sector 17 to be drawn along by the slider 3 whilst being able to rotate with respect thereto. Secondly, with its peripheral toothing, the pin 17b functions as a gearwheel that meshes with a respective toothing or rack 2a provided on one side of the slide 2, made simply as a prismatic guide that slides longitudinally through and with respect to the slider 3.

The radius of the external toothing 17a of the toothed sector 17 is greater than the radius of the toothing constituted by the external grooves of the pin 17b. Consequently, when the slider 3 is retracted (movement from the top downwards, as viewed in FIG. 6), the engagement of the toothing 17a with the rack 9 causes the toothed sector 17 to turn (in a counterclockwise direction, as viewed in FIG. 6) and cause a relative advance of the slide 2 with respect to the body of the slider 3. However, since the slider 3 in turn recedes under the action of the operator, the overall effect achieved will be a recession of the sheath G, connected to the slide 2, by an amount given by the difference between the recession of the slider 3 and the relative advance of the slide 2 with respect to the slider 3 itself. The amount of this relative advance is determined by the ratio between the radius of the toothing 17a and the radius of the grooved pin 17b, thus being selectable within a wide range of variation.

It will moreover be appreciated that the individual details of the embodiments described and illustrated herein with reference to a specific example of an embodiment may be freely transposed also to the other embodiments.

Naturally, the principle of the invention remaining the same, the forms of embodiment and the details of construction may vary widely with respect to what is described and illustrated herein, without thereby departing from the scope of the present invention.

What is claimed is:

1. An actuating device for a catheter comprising at least one first part and one second part, which are able to more relative to each other, the actuating device comprising:
   (i) a tubular slide which can be connected to one of said first part and said second part of the catheter;
   (ii) a slider, which is mobile with respect to the slide in the direction of a longitudinal axis and which can be actuated for moving said slide and moving said first part and said second part relative to each other; and
   (iii) a speed-change mechanism, which is set between said slider and said slide,
   wherein said speed-change mechanism is able to perform the transmission of the movement between said slider and said slide with at least two drive ratios that are different in successive parts of a movement of said first part and said second part relative to each other.

2. The device according to claim 1, wherein said speed-change mechanism comprises:
   (i) a member for transmission of motion, which co-operates with said slider and said slide for a part of said movement of said first and second parts relative to each other until one given position of said movement of said first and second parts relative to each other is reached it being possible for said member for transmission of motion to be disengaged from between said slider and said slide until said given position of said movement of said first and second parts relative to each other is reached; and
   (ii) complementary elements carried by said slider and by said slide, said complementary elements coming to bear upon one another substantially in a position corresponding to said given position of said movement of said first and second parts relative to each other, so as to obtain a ratio of drawing between said slider and said slide.

3. The device according to claim 2, wherein said speed-change mechanism comprises at least one rotating body between said slider and said slide and carried by one of said slider and said slide, and having a toothing which is able to engage a respective toothing provided in the said slider or said slide that does not carry the rotating body; said at least one rotating body likewise operating in a relationship of meshing with a further toothing carried by a part of a casing of said actuating device and, when said given position of said movement of said first and second parts relative to each other is reached, the toothing of said at least one rotating body disengages from at least one of said respective toothing and said further toothing.

4. The device according to claim 2, wherein said slide comprises an elongated body with a central core, and said slider has a general gantry-shaped confirmation with an actuation board and side parts slidably fitted on said elongated body of the slide and said complementary elements are constituted by said core of the slide and by one of said side parts of said slider.

5. The device according to claim 1, wherein said speed-change mechanism comprises at least one rotating body between said slider and said slide and carried by one of said slider and said slide, and having a toothing which is able to engage a respective toothing provided in the said slider or said slide that does not carry the rotating body; said at least one rotating body likewise operating in a relationship of meshing with a further toothing carried by a part of a casing of said actuating device.

6. The device according to claim 5, wherein said at least one rotating body is a wheel carried by one of said slider and said slide and having a peripheral toothing, which is able to engage both said respective tooting provided in the said slider or said slide that does not carry the rotating body and said further toothing carried by a part of a casing of said actuating device.

7. The device according to claim 5, wherein said at least one rotating body is a toothed sector carried by one of said slider and said slide and having a peripheral toothing that meshes with said further toothing carried by a part of said casing of said actuating device; said toothed sector being pivoted on a tooted pin, which is able to engage a respective tooting provided in the said slider or said slide that does not carry the rotating body.

8. The device according to claim 7, wherein said slider comprises a body that is able to move longitudinally with respect to said casing with said slide slidably mounted with respect to said body of the slider, and said toothed sector is pivoted on the body of the slider by said toothed pin, which meshes with said respective toothing provided on said slide.

9. The device according to claim 8, wherein associated to said slider is a projecting formation which can be used for moving said slider.

10. The device according to claim 1, wherein said speed-change mechanism comprises at least one element of transmission of motion in the form of a wheel carded by said slide, said wheel co-operating with a part of a casing of said device so as to guide the movement of said slide.

11. The device according to claim 1, wherein said slide comprises an elongated body with a central core, and said slider has a general gantry-shaped confirmation with an actuation board and side parts slidably fitted on said elongated body of the slide.

12. The device according to claim 1, wherein the device comprises a casing and said slider comprises a body that is able to move longitudinally with respect to said casing with said slide slidably mounted with respect to said body of the slider.

13. The device according to claim 12, wherein associated to said slider is a projecting formation which can be used for moving said slider.

14. The device according to claim 1, wherein the device comprises a casing with a slit to enable sliding for at least part of said slider, said slit enabling access to said slider to move said slider with respect to said slide.

15. An assembly comprising a catheter comprising at least one first part and one second part, which are able to move relative to each other, and an actuating device for the catheter comprising:

(i) a tubular slide which can be connected to one of said first part and said second part of the catheter;

(ii) a slider, which is mobile with respect to the slide in the direction of a longitudinal axis and which can be actuated for moving said slide and moving said first part and said second part relative to each other; and (iii) a speed-change mechanism, which is set between said slider and said slide, wherein said speed-change mechanism is able to perform the transmission of the movement between said slider and said slide with at least two drive ratios that are different in successive parts of a movement of said first part and said second part relative to each other, and wherein said slide is connected to one of said first part and said second part of the catheter.

* * * * *